US006130057A

United States Patent [19]

Gosnell et al.

[11] Patent Number: 6,130,057

[45] Date of Patent: Oct. 10, 2000

[54] METHOD FOR DIFFERENTIATING MICROORGANISMS IN A SAMPLE

[75] Inventors: C. Michael Gosnell, Fallston; Carrie A. Hughes, Parkton; Paul E. Goldenbaum, Hampstead, all of Md.

[73] Assignee: Becton, Dickinson and Company, Franklin Lakes, N.J.

[21] Appl. No.: 09/407,638

[22] Filed: Sep. 28, 1999

[51] Int. Cl.[7] ................................ C12Q 1/18; C12Q 1/04; C12Q 1/02

[52] U.S. Cl. .............................. 435/32; 435/968; 435/34; 435/29

[58] Field of Search ................................ 435/32, 968, 34, 435/29

[56] References Cited

PUBLICATIONS

Ashdown, L.. R.; "Pathology"; vol. 11(2), pp. 293–297, Feb. 1979.

Wu, William, G.; "Medical Microbiology"; 2nd Edition, pp. 349, 1989.

*Primary Examiner*—Louise N Leary
*Attorney, Agent, or Firm*—Bruce S. Weintraub, Esq.

[57] ABSTRACT

Culture media for microorganisms containing blood or hemin, particularly Trypticase Soy Agar with blood, and chocolate agar, are combined with known chromogenic substrates to produce chromogenic media. Methods for preparing these chromogenic media include adding chromogenic substrates to the surface of previously prepared media, or incorporating the chromogenic substrate into the media as it is prepared. Methods for distinguishing microorganisms in a sample using these culture media are also described.

39 Claims, No Drawings

METHOD FOR DIFFERENTIATING MICROORGANISMS IN A SAMPLE

BACKGROUND OF THE INVENTION

Differentiation and identification of microorganisms such as bacteria, fungi or yeasts in a sample suspected of containing pathogenic organisms is important. The non-pathogenic organisms must be distinguished from the pathogens. Most frequently, samples contain mixed bacteria, mixed fungi or mixed yeasts, whether a clinically obtained sample, or an environmental sample, e.g. from a water supply, or a food based sample, including poultry and dairy products.

While numerous methods have evolved to help distinguish and identify microorganisms, most involve appropriate selection of culture media and several additional steps including incubating, preliminary identification by morphology, followed by further culturing and incubation of selected microorganisms. In some instances, complete identification of the microorganisms in a sample can take several days, as the cultures are typically incubated for 18–24 hours before significant growth is detected.

By way of example, by formulating the culture media to permit the growth of only bacteria with certain characteristics, the growth of some bacteria (which are not of interest) can be suppressed. However, regardless of how culture media are adjusted, by altering ingredients or the concentrations of ingredients, selection of the culture media still may not typically result in clear identification and differentiation of all the bacterial species present in the sample. Microscopic examination of morphology and further testing are commonly required, or use of multiple, differing culture media.

Use of color to differentiate various microorganisms was attempted against this backdrop.

While use of color to differentiate and identify microorganisms has been known for many years, until recently, these methods suffered from many drawbacks, including deterioration of the color change, diffusion or evaporation of the color formed, generation of color which cannot distinguish between bacteria or which is difficult to read against the color of the media, or the necessity for several steps, including UV radiation to develop the color.

Relatively recently, so-called chromogenic media have been utilized to differentiate microorganisms.

The primary method employed by chromogenic media to detect and differentiate microorganisms is the reaction of glycosidase substrates, as shown below. This basic chemical reaction to form color is exemplified by X-Gal (5-bromo-4-chloro-3-indolyl-β-D-galactopyranoside), a reagent commonly used in molecular biology to monitor lacZ gene exprssion. This colorless substrate undergoes a reaction with galactosidase to produce an insoluble blue indigo product:

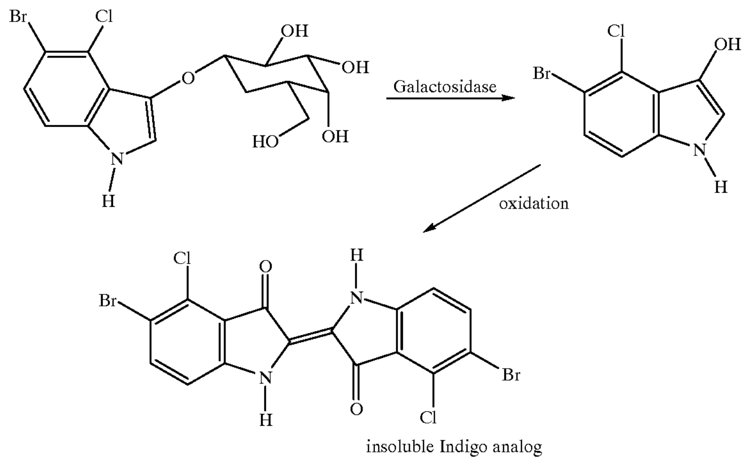

The oxidation step occurs rapidly to produce the indigo compound from the unstable 3-hydroxy indole. This oxidation may be air mediated and may also involve cellular metabolic processes in some organisms. One advantage of the indigo compounds as microbial indicators is their localization within the microorganisms, which helps to prevent deterioration and diffusion of the color change. The indigo compounds are also relatively nontoxic to growing microorganisms. Another advantage is that several colors are available by changing substituents on the indolyl ring. This allows differentiation of microorganisms with different glycosidase activities. A list of such colored substrate products is given below.

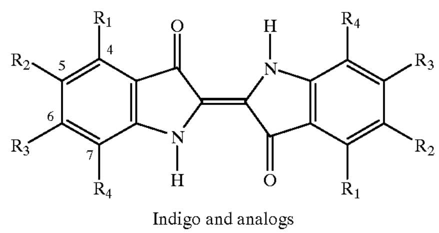

Indigo and analogs

Products of known indolyl glycoside substrates:

| $R_1$ | $R_2$ | $R_3$ | $R_4$ | Color |
|---|---|---|---|---|
| H | H | H | H | blue |
| Cl | Br | H | H | blue |
| H | Br | Cl | H | magenta |
| H | H | Cl | H | salmon |
| H | I | H | H | purple |
| H | Br | H | H | blue |

In addition to glycosidase substrates, dyes such as pH indicators are occasionally used in chromogenic media.

Chromogenic indolyl substrates for esterases, phosphatases, and other enzymes are also used in some applications. These work similarly to the glycosidase substrates. An example, "Mag-Phos" is shown below.

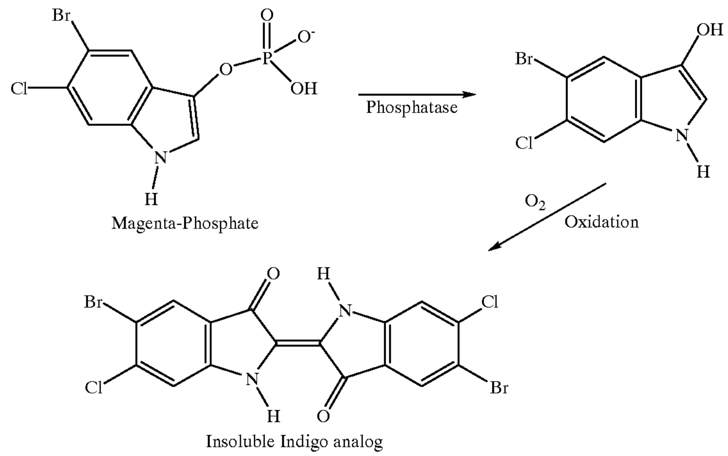

Recently, many examples of testing methods utilizing this basic chemistry have been reported, some of which are described below.

Rapid identification of Salmonella is an important public health issue. Culture media for this purpose comprising a chromogenic compound linked to a $C_7$–$C_{10}$ fatty acid, and an appropriate detergent which promotes liberation of the chromogenic compounds is proposed in WO94/09152. The chromogenic compound is preferably 5-bromo-4-chloro-3-indolyl caprylate, and the detergent is selected from fused polycyclic detergents. β-glucosides and/or β-galactosides are advantageously added.

Chromogenic compounds derived from indolylglucuronic acid as a substrate for the GUS enzyme are described in WO 94/08043.

Combining a chromogenic β-galactosidase and a β-galactosidase and a β-glucoronidase in a test medium to distinguish between *Escherichia coli* and general coliforms in a single test with a single sample is disclosed in U.S. Pat. No 5,210,022.

A test medium useful for identifying bacteria found in urine samples containing a chromogenic β-glucoronidase substrate capable of forming a first color when reacted with β-glucoronidase, a chromogenic arylsulfatase substrate capable of forming a second color when reacted with arylsulfatase, and a nutrient base is described in U.S. Pat. No. 5,464,755. Proteinaceous opaque compounds, such as milk-derived compounds can be included in the test medium. A medium for isolating Salmonella colonies without ambiguity by use of specific coloration is disclosed in U.S. Pat. No. 5,194,374. This medium contains peptones, a polyol metabolizable by Salmonella and a pH indicator sensitive to acidification. The polyol is adsorbed on a pulverulent material. The medium may also contain deoxycholate and a chromogenic β-galactosidase substrate.

A method for revealing the presence or absence of a particular microorganism strain, with at least one strain-specific enzyme substrate chromogen and at least one compound selected from a high concentration carbohydrate, are added to the culturing medium as disclosed in WO95/04156. Once the chromogen has been hydrolyzed, a color differing from the basic color of the chromophore results.

A method of identifying *E. coli* using a growth medium for *E. coli* with 8-hydroquinoline-β-D-glucuronide as an activator such as X-glucuronide is disclosed in EP 0025467. This method shows the *E. coli* as darkly pigmented blobs.

Determining the presence of *E. coli* in a liquid sample passed through a suitable membrane filter by contacting the filter with a chromogenic reagent, indoxyl-β-D-Glucuronide, in an *E. coli* nutrient medium followed by incubation is described in U.S. Pat. No. 4,923,804. The *E. coli* appears as an indigo blue color.

A method for identifying Enterobacteriaceae in a single culture medium is disclosed in U.S. Pat. No. 3,870,601. The media comprises a mixture of chromogenic β-galactoside substrates with a decarboxylase substrate, a deaminase substrate, a urease subtrate, a hydrogen disulfide detection system, or a carbohydrate fermentation system. ONPG (o-nitrophenyl-β-galactopyranoside) is disclosed as suitable.

Use of two different chromogens, and biological material capable of fermenting a sugar in a test medium adjusted to a pH conducive for color change of a pH indicator upon acidification upon fermentation of the sugar, is used to distinguish bacteria in WO 97/36001.

Direct detection of Salmonella (except *S. arizonae*) is possible by combining glucuronic acid and a pH indicator in the culture medium, together with a chromogenic or fluorogenic compound capable of being hydrolyzed by β-galactosidase, as described in U.S. Pat. No. 5,434,056.

WO96/40861, like other art, is concerned with the identification of pathogens such as the possibly fatal *E.coli* 0157:H7 and Salmonella. A medium, liquid or solid, containing propionic acid, one or more chromogenic substrates, such as galactosidase substrates and glucuronidase substrates, and a nutrient base can identify these bacteria, according to this document.

Differentiation of pathogenic monocytogenes species of Listeria from the non-pathogens by use of a glycine amino peptidase substrate is disclosed in U.S. Pat. No. 5,330,889. Identification and differentiation of different species of yeasts can be accomplished using CHROMagar Candida plates available from CHROMagar Company, Paris, France. Yeasts from clinical samples grown on these plates are identified by variant colors and morphology. See e.g. A. P. Koehler, et al. *J. Clin. Microbiol.*, 37, pp. 422–26 (1999). The CHROMagar medium is composed of 10 g peptone, 20 g glucose, 15 g agar, 0.5 g chloramphenicol, per liter, and a "chromogenic mixture," whose components are maintained in secrecy by the manufacturer. (E. T. S. Houang, et al., *J. Clin. Path.*, 50, pp. 563–565 (1997).) The yeast colonies appear in colors such as pink, blue, apple green and rose on a clear background.

CHROMagar Salmonella (CAS) is used to identify Salmonella spp. as mauve colonies after 18 hours of incubation, while other members of the Enterobacteriaceae grow as blue or uncolored colonies. (O. Gaillot, et al., *J. Clin. Microbiol*., 37, pp. 762–65 (1999).)

While there are obviously many methods known and described for differentiating microorganisms, those currently known involve the use of culture media which are clear, thus providing good contrast and ready visibility when a color change takes place. Use of opaque media have also been used with chromogens, such as resulting from the addition of proteinaceous materials such as milk. Here again, however, the color change of susceptible bacteria is easy to detect.

Not all clinically important bacteria, yeasts or fungi can be cultured on the chromogenic media described above. For example, the so-called fastidious bacteria have specific growth requirements, and will not grow, (or grow in a meaningful way) on routine media. Examples of clinically important fastidious bacteria include Neisseria and Haemophilus. Many of these bacteria are found in respiratory, cerebral-spinal and genital fluids and secretions.

For these fastidious bacteria, incubation and growth is normally performed on chocolate agar, a culture medium containing hemoglobin. (See, Martin et al., Publ. Health Rep., 82:361 (1967). As its name implies, chocolate agar looks like chocolate and is brown in color. Therefore, whether chromogenic media will provide any meaningful contrast to permit differentiation and identification of bacteria is unknown.

Trypticase Soy Agar (TSA) with sheep blood is a culture media which is commonly used for the cultivation and isolation of fastidious microorganisms when distinct hemolytic reactions are important (e.g., *Streptococcus pneumomiae* from respiratory specimens). This culture media supports growth of many kinds of bacteria, which can only be distinguished by their morphology, which may be extremely difficult. Due to the presence of the blood, this media has a bright red color, and therefore it is unknown whether a color change would be discernible on this media.

The TSA with sheep blood media differentiates microorganisms on the basis of hemolysis, which results in the clearing (or lysis) of red blood cells due to the production of hemolysins by the microorganisms.

Due to their dark color it was unknown whether chromogenic reactions would be discernable on TSA and blood or chocolate agar plates. Moreover, it was unknown whether the presence of chromogens in the media would interfere with the hemolytic reaction on TSA with sheep blood media.

It is an object of this invention to prepare a chromogenic indicator medium containing blood or hemin for growing and identifying microorganisms.

It is another object of the present invention to prepare a TSA and sheep blood culture medium containing chromogenic substrates.

It is also an object of the present invention to differentiate microorganisms based on a change in color of the microorganisms on a TSA and sheep blood culture medium.

Another object of the present invention is to prepare a chocolate agar culture medium containing chromogenic substrates.

Yet another object of this invention is to differentiate bacteria based on a change in color of the bacteria on chocolate agar media.

SUMMARY OF THE INVENTION

The present invention relates to a method for differentiating microorganisms in a sample utilizing a chromogenic indicator medium containing blood or hemin for growing and identifying microorganisms.

The present invention also encompasses a method for utilizing a chromogenic indicator media for color differentiating microorganisms, including bacteria, yeasts and fungi, in a culture medium containing blood or hemin such as Trypticase Soy Agar with 5% Sheep Blood (TSASB), or Chocolate agar. Other dye or color producing compounds, such as crystal violet, could be used in the media as well. The resulting chromogenic reactions are visible and easily readable on these non-clear, i.e., colored growth media. Surprisingly, the presence of the chromogens do not adversely affect the other differential properties of the growth media, such as hemolytic reactions, colony size or shape or other characteristics. This invention can be used for clinical and industrial (e.g. food, water, environmental or pharmaceutical) specimens, and includes a method for differentiating bacteria on TSASB and Chocolate agar growth media with chromogens. The invention also includes methods for preparing chromogenic indicator media containing blood or hemin.

DETAILED DESCRIPTION OF THE INVENTION

The present invention uses chromogens in conjunction with known growth media TSASB and chocolate agar.

TSASB is commercially available. For example, premade plates containing this growth media can be obtained from Becton Dickinson Biosciences, Cockeysville, Md., under the name TSA II™. Such plates are normally stable, under refrigeration, for 14–16 weeks.

Alternatively, TSASB can be made in according to known formulas and procedures. See, e.g. Dilworth, et al., J. Clin. Microbiol., 2:453 (1975).

Chocolate agar growth media are also commercially available, pre-plated and in tubed slants, from manufacturers such as Becton Dickinson Biosciences, Cockeysville, Md., under the name Chocolate Agar II.

Chocolate agar can also be made according to known formulas and procedures. See, e.g. Martin et al., Publ. Health Rep., 82:361 (1967).

As discussed in the Background herein, suitable chromogenic substrates are compounds which will be acted upon by enzymes found in the target bacteria to result in an insoluble colored product which is contained within the bacteria. Many such chromogenic substrates are known and each is targeted to a specific enzyme.

Examples of suitable chromogenic substrates are provided below. This listing is not meant to be all-inclusive. Other such compounds are known, and are available from companies such as Sigma (St. Louis, Ill.), INALCO (Milan, ITALY), BIOSYNTH (AG Staad, SWITZERLAND), BIOSYNTH INTERNATIONAL (Naperville, Ill.) and GLYCOSYNTH (Warrington, Cheshire, England).

| Abbreviation | Chemical Name |
|---|---|
| X-Acglmn | 5-Br-4-Cl-3-indolyl-N-Acetyl-β-D-galactosaminide |
| X-Cap | 5-Br-4-Cl-3-indolyl-caprylate |
| BG-Gal | 4-Cl-3-indolyl-β-D-galactopyranoside |
| Sal-Gal | 6-Cl-3-indolyl-β-D-galactopyranoside |
| X-Gal | 5-Br-4-Cl-3-indolyl-β-D-galactopyranoside |

-continued

| Abbreviation | Chemical Name |
|---|---|
| X-Glucoside | 5-Br-4-Cl-3-indolyl-β-D-glucopyranoside |
| Sal-Glucuro | 6-Cl-3-indolyl-β-D-glucuronide (CHA salt) |
| X-Gluc | 5-Br-4-Cl-3-indolyl-β-D-glucuronide (CHA salt) |
| X-Glucuro (c) | 5-Br-4-Cl-3-indolyl-β-D-glucuronide (CHA salt) |
| X-Glucuro (s) | 5-Br-4-Cl-3-indolyl-β-D-glucuronide (sodium salt) |
| IPTG | Isopropyl-β-D-thiogalactopyranoside |
| Mag-Phos | 5-Br-6-Cl-3-indolyl-phosphate, p-touidine salt |
| X-Sulfate | 5-Br-4-Cl-3-indolyl-sulfate (Potassium salt) |
| X-α-Glucoside | 5-Br-4-Cl-3-indolyl-α-D-glucopyranoside |
| X-Cello | 5-Br-4-Cl-3-indolyl-β-D-cellobioside |
| X-Acetate | 5-Br-4-Cl-3-indolyl-3-acetate |
| X-Glucosamine | 5-Br-4-Cl-3-indolyl-β-D-glucosaminide |
| X-Butyrate | 5-Br-4-Cl-3-indolyl-butyrate |
| X-Palminate | 5-Br-4-Cl-3-indolyl-palminate |
| X-Phosphate | 5-Br-4-Cl-3-indolyl-phosphate |
| X-Fucoside | 5-Br-4-Cl-3-indolyl-β-D-fucoside |
| X-Xylo | 5-Br-4-Cl-3-indolyl-β-D-xylopyranoside |

Chromogenic substrates, such as those noted above, can be added to the growth media in at least two ways.

A small amount of the chromogenic substrate, from 0.05 to 0.2 g, preferably 0.05 to 0.1 g (e.g. 0.08 g) can be added to a small amount of DMSO (e.g. 1 ml.). Then a small aliquot of this solution (e.g. about 50 microliters) can be added to the surface of a pre-plated medium, either TSASB or chocolate agar, then distributed using a spreader. The plate is then allowed to dry 3–4 hours in a hood. It will be noted that in some instances a powdery insoluble precipitate forms during spreading.

Another method of incorporating the chromogenic substrates into the growth media is to freshly prepare the media in accordance with known procedures. All chromogens can be added aseptically to the base post autoclaving at a preferred concentration of 0.1 g/l (a suitable range is 0.05 to 0.20 g/l ). Chromogens are either pre-dissolved in DMSO or added as powder, if water soluble. Chromogens can also be added prior to autoclaving.

Other methods for incorporating the chromogenic substrates will be apparent to those of ordinary skill in the art.

The fungi which may be used in the present invention are those known to one of ordinary skill in the art and include Aspergillus spp., Trichosporn spp. and Geotrichum spp. Likewise, yeasts which may be evaluated in the present invention are known to those of ordinary skill and include Candida spp. and Cryptoccus spp.

The bacteria to be grown and differentiated using the present invention are those which are known to be suitable for growth on blood or hemin containing media. As noted previously, fastidious bacteria are intended for the Chocolate agar medium. Examples include Haemophilus spp. and Neisseriae spp.

Sources of such bacteria include clinical samples, such as sputum, urine and blood and industrial sources, such as food, water, environmental or pharmaceutical samples.

TSASB suitable bacteria are also well known. Examples are *Streptococcus pneumoniae, Streptococcus pyogenes*, and *Streptococcus agalactiae.*

Samples of suitable bacteria for TSASB can be obtained from many sources, including clinical samples and industrial samples.

Of course, as is well known, specific, identified bacteria can be obtained from sources such as ATCC, the American Type Culture Collection in Manassas, Va.

Specific examples of the use of various chromogenic substrates on both TSASB and chocolate agar media are provided below. The specific experiments set forth below demonstrate that various bacteria respond differently to the presence of chromogenic substrates.

Some bacteria will develop a color, such as dark blue, green or pink, that will differentiate them, perhaps in combination with a characteristic morphology, from other bacteria in a sample. In some cases, a particular bacteria may remain colorless, while others of the same species do develop color, thus providing another basis to differentiate the bacteria. Yet another possibility is that a particular bacterium will develop a color different from those of other bacteria in a sample. This provides yet another means for the bacteria to be differentiated from other bacteria in a sample.

EXAMPLE 1

In this series of experiments, 0.08 g of each chromogen indicated below was added to 1.0 ml DMSO and thoroughly mixed. All the chromogens appeared to be soluble, providing a clear and/or colorless solution, except for Mag-Phos, which appeared clear and light orange in color.

| Abbreviation | Chemical Name |
|---|---|
| X-Acglmn | 5-Br-4-Cl-3-indolyl-N-Acetyl-β-D-galactosaminide |
| X-Cap | 5-Br-4-Cl-3-indolyl-caprylate |
| BG-Gal | 4-Cl-3-indolyl-β-D-galactopyranoside |
| Sal-Gal | 6-Cl-3-indolyl-β-D-galactopyranoside |
| X-Gal | 5-Br-4-Cl-3-indolyl-β-D-galactopyranoside |
| X-Glucoside | 5-Br-4-Cl-3-indolyl-β-D-glucopyranoside |
| Sal-Glucuro | 6-Cl-3-indolyl-β-D-glucuronide (CHA salt) |
| X-Glucuro (c) | 5-Br-4-Cl-3-indolyl-β-D-glucuronide (CHA salt) |
| X-Glucuro (s) | 5-Br-4-Cl-3-indolyl-β-D-glucuronide (sodium salt) |
| IPTG | Isopropyl-β-D-thiogalactopyranoside |
| Mag-Phos | 5-Br-6-Cl-3-indolyl-phosphate, p-touidine salt |
| X-Sulfate | 5-Br-4-Cl-3-indolyl-sulfate (Potassium salt) |

50 μl of each chromogen solution was added to the surface of each of the following pre-plated media (one chromogen solution per plate):

TSAII 5% Sheep Blood;

Chocolate II; and

TSA plain (no blood).

All pre-plated media were obtained from Becton-Dickinson Microbiology Systems, MD.

The solution was dispersed using a spreader and allowed to dry 3–4 hours in a hood. In some instances a powdery, insoluble precipitate formed during spreading, except for X-Glucuro(s) which remained clear. After 1 week, however, some precipitate was evident only on the X-Glucoside and X-Acglmn plates.

The bacterial test strains were adjusted to a 0.5 McFarland equivalent and diluted 1:10 in sterile saline. The plates were then inoculated using the standard streak plate method.

The following bacteria were evaluated: *Escherichia coli* 25922*; Staphylococcus aureus* 25923*; S. epidermidis* 12228*; Streptococcus pneumoniae* 6303*; Group B Strep.* 12386*; Haemophilus influenzae* 35540, 10211*; Branhamella catarrhalis* 25238*; Neisseria meningitidis* 13090*; N. sicca* 29193*; N. gonorrhoeae* 35201; and *Gardnerella vaginalis* 14019.

All plates were incubated at 35° C. for 20–24 hours. The TSAII with Sheep blood and TSA II (plain) were incubated in air, while the chocolate agar was incubated in $CO_2$ (5%).

After incubation, the plates were evaluated for growth by quadrant readable colonies.

The fastidious strains of bacteria were only tested on Chocolate II Agar. Results of these tests are presented below in Tables I and II.

TABLE I

Evaluation of Microorganism Colony Color Formation Following Growth on TSA II With 5% Sheep Blood, TSA plain and Chocolate II Agar Supplemented With Various Chromogenic Substrates

| | | TSA Plain | | TSA II 5SB | | Choc II | |
|---|---|---|---|---|---|---|---|
| Test Strain | Substrate | Growth | Color | Growth | Color | Growth | Color |
| *S. epi* 12228 | X-Acglmn | 4+ | WT | 4+ | WT | 4+ | WT |
| | X-Cap | NG | NA | 1+ | WT | NG | NA |
| | X-Gal | 1+ | WT | 4+ | WT | 4+ | WT |
| | X-Glucoside | 4+ | WT | 4+ | WT | 4+ | WT |
| | X-Glucuro | 4+ | WT | 4+ | WT | 4+ | WT |
| | Mag-phos | 1+ | purple | 1+ | purple | 1+ | purple |
| *E. coli* 25922 | X-Acglmn | 4+ | NC | 4+ | NC | 4+ | NC |
| | X-Cap | 4+ | NC | 4+ | NC | 4+ | NC |
| | X-Gal | 4+ | blue | 4+ | blue | 4+ | blue |
| | X-Glucoside | 4+ | NC | 4 | NC | 4+ | NC |
| | X-Glucuro | 4+ | blue | 4+ | blue | 4+ | blue |
| | Mag-Phos | 4+ | purple | 4+ | purple | 4+ | purple |
| *S. aureus* 25923 | X-Acglmn | 4+ | NC | 4+ | NC | 4+ | NC |
| | X-Cap | 1+ | turquoise | 4+ | turquoise (mixed) | 4+ | turquoise mixed |
| | X-Gal | 4+ | NC | 4+ | NC | 4+ | NC |
| | X-Glucoside | 4+ | NC | 4+ | NC | 4+ | NC |
| | X-Glucuro | 4+ | NC | 4+ | NC | 4+ | NC |
| | Mag-Phos | 1+ | purple | 3+ | purple | 2–3+ | purple |
| *S. pneu*: 6303 | X-Acglmn | 1+= | NC | 4+= | blue | 4+= | NC |
| | X-Cap | NG | NA | < | NC | NG | NC |
| | X-Gal | = | NC | = | light blue | = | NC |
| | X-Glucoside | < | NC | = | NC | = | NC |
| | X-Glucuro | = | NC | = | NC | = | NC |
| | Mag-Phos | NG | NA | < | NC | < | NC |
| *B. catt* 25258 | X-Acglmn | = | NC | = | NC | = | NC |
| | X-Cap | NG | NA | < | NC | < | NC |
| | X-Gal | NG | NA | = | NC | = | NC |
| | X-Glucoside | < | NC | = | NC | = | NC |
| | X-Glucuro | >> | NC | = | NC | = | NC |
| | Mag-phos | NG | NA | << | NC | NG | NC |
| Group B Strep 12386 | X-Acglmn | = | NC | = | NC | = | NC |
| | X-Cap | NG | NA | < | NC | << | NC |
| | X-Gal | < | NC | < | NC | = | NC |
| | X-Glucoside | = | blue | = | blue | = | blue |
| | X-Glucuro | = | blue | = | blue (a) | = | blue |
| | Mag-phos | < | purple | < | purple (a) | = | purple |

| | Substrates on Chocolate II Agar | | | | | |
|---|---|---|---|---|---|---|
| Test Strain | X-Acglmn | X-Cap | X-Gal | X-Glucoside | X-Glucuro | Mag-Phos |
| *H. influ.* 35540 | = NC | = NC | = NC | = NC | = NC | = purple |
| *N. gono.* 35201 | = NC | NG | < NC | < NC | NG | NG |
| *G. vag.* 14019 | = NC | NG | = NC | < NC | NG | NG |

TABLE I-continued

| Evaluation of Microorganism Colony Color Formation Following Growth on TSA II With 5% Sheep Blood, TSA plain and Chocolate II Agar Supplemented With Various Chromogenic Substrates | | | | | | |
|---|---|---|---|---|---|---|
| *H. influ.* 10211 | = NC | NG | = NC | = NG | = NC | = purple |
| *N. sicca.* 29193 | = NC | blue | = NC | = NC | = NC | = purple |
| *N. mening.* 13090 | < NC | NG | = NC | = NC | = NC | = NC |

Key:
NC = no Color
a = not as hemolytic
NG = no growth
WT = white
NA = not applicable
= growth equivalent to control sample
< colony size/quadrant less

TABLE II

Summary of Table I Results

| Test Strains | Substrates Producing Color | Substrates Producing Growth Inhibition |
|---|---|---|
| *E. coli* 25922 | X-Gal, X-Glucuro, Mag-phos | None |
| *S. aureus* 25923 | X-Cap, Mag-phos | None |
| *S. epidermidis* 12228 | Mag-phos | X-Cap |
| *S. pneumoniae* 6303 | X-Acglmn (TSA II only) | X-Cap, Mag-phos |
| Group B Strep. 12386 | X-Glucoside, X-Glucuro, Mag-phos | Slight inhib. W/ X-Cap, X-Gal, Mag-phos |
| *H. influenzae* 35540, 10211 | Mag-phos | None |
| *B. catarrhalis* 25238 | None | X-Cap, Mag-Phos |
| *N. meningitidis* 13090 | None | Slight inhib w/ X-Acglmn |
| *N. sicca* 29193 | X-cap, Mag-phos | None |
| *N. gonorrhoeae* 35201 | None | X-Cap, X-Glucuro, Mag-phos |
| *G. vaginalis* 14014 | None | X-Cap, X-Gal, X-Glucuro, Mag-phos |

It was surprising to discover that chromogenic substrates dissolved in the organic solvent dimethylsulfoxide (DMSO), when applied to the surface of or incorporated within a highly colored medium (i.e., a medium containing blood or hemin) could support the growth of microorganisms and result in color differentiation of the microorganisms.

The *Haemophilus influenzae*, both strains, appear dark purple on chocolate agar with Mag-phos. This is clearly differentiated from other sputum normal flora which appeared non-colored.

Group B streptococcus appears blue with beta hemolysis on TSASB with X-Glucuro.

*Neisseria sicca* appears purple on Chocolate agar with Mag-phos. *N. meningitidis* appears colorless.

In conducting these experiments, it was found that X-Cap and Mag-phos were somewhat insoluble, forming a white precipitate, when placed on the plated media. These two compounds also proved to have the most inhibitory effect. It is possible the concentration used for these compounds was too high.

EXAMPLE 2

Using the procedure of Example 1, the bacteria tabulated below were evaluated on TSA II 5% Sheep Blood and Chocolate II agar. In each instance, the chromogens were added to the surface of the prepared-plated media at 0.004 g/plate in 50 $\mu$l DMSO. The following bacteria were evaluated: *Branhamella catarrhalis; Clostridium jejuni; Clostridium perfringens; Escheria coli; Enterococcus faecalis*, Peptostreptococcus spp.; *Streptococcus agalactiae; Staphylococcus aureus; Staphylococcus epidermidis; Streptococcus mitis; Streptococcus pneumoniae; Streptococcus pyogenes*; and Streptococcus groups C, F and G.

The results of this experiment, designed to evaluate the effect of growth conditions (incubation) on colony color formation, are tabulated below:

TABLE III

TSA II 5% Sheep Blood (chromogens added to surface at 0.004 g/plate in 50 $\mu$l DMSO)

| Strain | Reference No. | Incubation Conditions | X-Acglm | X-Cap | X-Gal | X-Glucoside | X-Glucuro | Mag-Phos |
|---|---|---|---|---|---|---|---|---|
| *B. catarrhalis* | 25258 | 24 h, $CO_2$ | NC | NC | NC | NC | NC | NG |
| *C. jejuni* | 33291 | 5 d, MA | NC | NG | NC | NC | NC | NG |
| *C. jejuni* | 33292 | 5 d, MA | NC | NG | NC | NC | NC | NG |
| *C. perfringens* | 13124 | 5 d, ANA | blue (l) | NG | blue (m) | NC | NC | NG |
| *E. coli* | 25922 | 24 h, air | NC | NC | blue (d) | NC | blue (d) | purple (m) |
| *E. coli* | 25922 | 5 d, ANA | NC | NC | blue (d) | NC | blue (m) | purple (m) |
| *E. coli* | 25922 | 5 d, MA | NC | NC | blue (d) | NC | blue (m) | purple (m) |
| *E. faecalis* | 29212 | 24 h, $CO_2$ | NT | NT | NT | NT | NC | NT |
| Peptostrep. spp | 27337 | 5 d, ANA | NC | NG | NC | NC | NC | NG |

TABLE III-continued

| TSA II 5% Sheep Blood (chromogens added to surface at 0.004 g/plate in 50 μl DMSO) | | | | | | | | |
|---|---|---|---|---|---|---|---|---|
| Strain | Reference No. | Incubation Conditions | X-Acglm | X-Cap | X-Gal | X-Glucoside | X-Glucuro | Mag-Phos |
| *S. agalactiae* | 4768 | 24 h, $CO_2$ | NT | NT | NT | NT | blue (l) | NT |
| *S. agalactiae* | 6638 | 24 b, $CO_2$ | NT | NT | NT | NT | blue (m) | NT |
| *S. agalactiae* | 12386 | 24 h, $CO_2$ | NC | NC | NC | blue (d) | blue (d) | purple (m) |
| *S. agalactiae* | 12386 | 24 h, $CO_2$ | NT | NT | NT | NT | blue (d) | NT |
| *S. agalactiae* | 13813 | 24 h, $CO_2$ | NT | NT | NT | NT | blue (d) | NT |
| *S. agalactiae* | BD11586 | 24 h, $CO_2$ | NT | NT | NT | NT | NC | NT |
| *S. agalactiae* | BD747 | 24 h, $CO_2$ | NT | NT | NT | NT | grey blue | NT |
| *S. aureus* | 25923 | 24 h, air | NC | blue (l) | NC | NC | NC | purple (m) |
| *S. epidermidis* | 12228 | 24 h, air | NC | NC | NC | NC | NC | purple (m) |
| *S. mitis* | 6249 | 24 h, $CO_2$ | blue (vl) | NT | NT | NT | NT | NT |
| *S. pneumoniae* | 6303 | 24 h, $CO_2$ | blue (l) | NC | blue (l) | NC | NC | NC |
| *S. pyogenes* | 19615 | 24 h, $CO_2$ | NT | NT | NT | NT | NC | NT |
| Strep Grp C | 12388 | 24 h, $CO_2$ | NT | NT | NT | NT | blue (d) | NT |
| Strep Grp F | 12392 | 24 h, $CO_2$ | NT | NT | NT | NT | NC | NT |
| Strep Grp F | BD77 | 24 h, $CO_2$ | NT | NT | NT | NT | NC | NT |
| Strep Grp G | 12394 | 24 h, $CO_2$ | NT | NT | NT | NT | grey blue (l) | NT |
| Strep Grp G | 27961 | 24 h, $CO_2$ | NT | NT | NT | NT | blue (d) | NT |

Abbrev:
NC = No Color
24 h = 24 hours
NT = Not Tested
5 d = 5 days
NG = no growth
$CO_2$ = 5% $CO_2$
vl = very light
MA = microaerophilic; 5–12% $CO_2$ and 5–15% $O_2$
l = light
ANA = anaerobic
m = medium
d = dark

TABLE IV

| Chocolate II Agar (chromogens added to surface at 0.004 g/plate in 50 μl DMSO | | | | | | | | |
|---|---|---|---|---|---|---|---|---|
| Strain | Reference No. | Incubation Conditions | X-Acglm | X-Cap | X-Gal | X-Glucoside | X-Glucuro | Mag-Phos |
| *B. catarrhalis* | 25258 | 24 h, $CO_2$ | NC | NC | NC | NC | NC | NG |
| *E. coli* | 25922 | 24 h, air | NC | NC | blue (d) | NC | blue (d) | purple (m) |
| *E. faecalis* | 29212 | 24 h, $CO_2$ | NT | NT | NT | NT | NC | NT |
| *G. vaginalis* | 14019 | 24 h, $CO_2$ | NC | NG | NG | NC | NG | NG |
| *H. influenzae* | 10211 | 24 h, $CO_2$ | NC | NC | NC | NC | NC | purple (m) |
| *H. influenzae* | 35540 | 24 h, $CO_2$ | NC | NC | NC | NC | NC | purple (m) |
| *N. gonnorhoeae* | 35201 | 24 h, $CO_2$ | NC | NG | NC | NC | NG | NG |
| *N. meningitidis* | 13090 | 24 h, $CO_2$ | NC | NG | NC | NC | NC | NC (col dark) |
| *N. sicca* | 29193 | 24 h, $CO_2$ | NC | blue (m) | NC | NC | NC | purple (m) |
| *S. agalactiae* | 4768 | 24 h, $CO_2$ | NT | NT | NT | NT | blue (l) | NT |
| *S. agalactiae* | 6638 | 24 h, $CO_2$ | NT | NT | NT | NT | blue (m) | NT |
| *S. agalactiae* | 12386 | 24 h, $CO_2$ | NC | NC | NC | blue (d) | blue (d) | purple (m) |
| *S. agalactiae* | 12386 | 24 h, $CO_2$ | NT | NT | NT | NT | blue (d) | NT |
| *S. agalactiae* | 13813 | 24 h, $CO_2$ | NT | NT | NT | NT | blue (d) | NT |
| *S. agalactiae* | BD11586 | 24 h, $CO_2$ | NT | NT | NT | NT | blue (vl) | NT |
| *S. agalactiae* | BD747 | 24 h, $CO_2$ | NT | NT | NT | NT | blue (l) | NT |
| *S. aureus* | 25923 | 24 h, air | NC | blue (l) | NC | NC | NC | purple (m) |
| *S. epidermidis* | 12228 | 24 h, air | NC | NG | NC | NC | NC | purple (m) |
| *S. mitis* | 6249 | 24 h, $CO_2$ | NC | NT | NT | NT | NT | NT |
| *S. pneumoniae* | 6303 | 24 h, $CO_2$ | NC | NG | NC | NC | NC | NC |
| *S. pyogenes* | 19615 | 24 h, $CO_2$ | NT | NT | NT | NT | NC | NT |
| Strep Grp C | 12388 | 24 h, $CO_2$ | NT | NT | NT | NT | blue (d) | NT |
| Strep Grp F | 12392 | 24 h, $CO_2$ | NT | NT | NT | NT | NC | NT |
| Strep Grp F | BD77 | 24 h, $CO_2$ | NT | NT | NT | NT | NC | NT |

TABLE IV-continued

| Chocolate II Agar (chromogens added to surface at 0.004 g/plate in 50 μl DMSO | | | | | | | | |
|---|---|---|---|---|---|---|---|---|
| Strain | Reference No. | Incubation Conditions | X-Acglm | X-Cap | X-Gal | X-Glucoside | X-Glucuro | Mag-Phos |
| Strep Grp G | 12394 | 24 h, $CO_2$ | NT | NT | NT | NT | blue (d) | NT |
| Strep Grp G | 27961 | 24 h, $CO_2$ | NT | NT | NT | NT | blue (d) | NT |

Abbrev:
NC = No Color
$CO_2$ = 5% $CO_2$
NT = Not Tested
NG = no growth
vl = very light
l = light
m = medium
d = dark As will be observed from a review of the data tabulated above, X-Acglmn and X-Gal may be useful to differentiate *C. perfringens* from other Clostridia spp. grown under microaerphilic or anaerobic conditions. Also, X-Gal, X-Glucurono and Mag-Phos may be used to differentiate *E. coli* grown under microaerophilic or anerobic conditions, in addition to ambient air conditions.

EXAMPLE 3

In this series of experiments, the chromogenic substrates were added directly into the culture medium as it was being prepared and prior to distribution to plates.

Laboratory prepared media consisting of TSA II base and 5% sheep blood were prepared in accordance with the procedures set out in Manual of BBL® Products and Laboratory Procedures, 4th ed., D. A. Power and P. J. McCuen (eds.), 1988. All chromogens were added aseptically to the base post autoclaving at a concentration of 0.1 g/l of media. Chromogens were either added as a powder (if water soluble) or predissolved in DMSO. In one instance, chromogens were added before autoclaving.

The chromogenic substrates used are set forth below:

In construing the chart below:
X=5-bromo-4-chloro-3-indolyl
Mag=5-bromo-6-chloro-3-indolyl
Sal=6-chloro-3-indolyl

| Chromogenic Substrate | Abbr. |
|---|---|
| X-N-Acetyl-β-D-galactosaminide | X-Acglmn |
| Magenta-caprylate | M-Cap |
| X-galactopyranoside (X-gal) + IPTG | X-Gal + IPTG |
| X-galactopyranoside | X-Gal |
| X-glucoside | X-Glucoside |
| Sal-glucuronide | Sal-Glucuro |

-continued

| Chromogenic Substrate | Abbr. |
|---|---|
| Magenta-phosphate | Mag-Phos |
| X-Sulfate | X-Sulf |
| X-Glucuronide | X-Glucuro |
| Mix (Sal-Glucuro, Mag-phos, X-Acglmn, BG-Gal) | Mix |
| TSA II 5% SB - no chromogens | TSA cont. |

A total of 55 strains (abbreviations as defined in Table V) were tested using the above media. Plates were incubated in $CO_2$ and air, or $CO_2$ only. All plates were read at 18–24 h for color, hemolytic activity, and growth as compared to the non-chromogenic control.

Colors were evaluated using Pantone Equivalents in order to more precisely and consistently identify the resulting colors, as noted below

| Color | Pantone Equivalent |
|---|---|
| b = blue | 17-4336 → 19-4340 |
| gb = grey blue | 17-4412 |
| p = purple | 18-3513 |
| gp = grey purple | 15-3807 |
| pb = purple blue | 18-3932 |
| NG = no growth | |

Used in front of the color abbreviations noted above, d=dark; l=light; vl=very light.

The bacterial strains were prepared in normal saline at 0.5 McFarland and diluted 1 in 10.

The plates were inoculated using the standard streak plate method or using a Steers replicator. Steers, E. et al., *Antibiot. Chemother.*, 9:307–311 (1959).

Results are tabulated below in Tables V and VI.

TABLE V

| Colony Color on Various Chromogenic TSA II with 5% Sheep Blood (Summary) | | | | | | | | | |
|---|---|---|---|---|---|---|---|---|---|
| | | No. | Chromogens | | | | | | |
| Strain | Abbrev. | Tested | X-Acglmn | X-Gal | X-Glucoside | X-Glucuro | Mag-phos | M-Cap | X-Sulf |
| *Aeromonas hydrophilia* | aehy | 3 | + | 0 | v | 0 | + | 0 | 0 |
| *Branhamella catarrhalis* | brca | 2 | 0 | 0 | 0 | 0 | v | 0 | 0 |
| *Candida albicans* | caal | 2 | + | 0 | 0 | 0 | 0 | 0 | 0 |

TABLE V-continued

| Colony Color on Various Chromogenic TSA II with 5% Sheep Blood (Summary) | | | | | | | | | |
|---|---|---|---|---|---|---|---|---|---|
| | | No. | Chromogens | | | | | | |
| Strain | Abbrev. | Tested | X-Acglmn | X-Gal | X-Glucoside | X-Glucuro | Mag-phos | M-Cap | X-Sulf |
| *Citrobacter freundii* | cifr | 2 | 0 | + | 0 | 0 | 0 | 0 | + |
| *Entercoccus faecalis* | enfa | 6 | + | v | + | 0 | + | 0 | 0 |
| *E. faecium* | enfu | 1 | + | + | + | 0 | + | 0 | 0 |
| *E. coli* (non-0157) | esco | 3 | 0 | + | 0 | + | v | 0 | 0 |
| *Klebsiella pneumoniae* | klpn | 3 | 0 | + | + | 0 | v | 0 | 0 |
| *Pseudomonas aeruginosa* | psae | 3 | 0 | 0 | v | 0 | 0 | 0 | 0 |
| Salmonella spp. | sasp | 2 | 0 | 0 | 0 | 0 | + | 0 | 0 |
| *Serratia marcescens* | sema | 1 | + | + | + | 0 | 0 | 0 | 0 |
| *Streptococcus agalactiae* | stag | 3 | 0 | 0 | + | 0 | + | 0 | 0 |
| *Staphylococcus aureus* | stau | 5 | 0 | 0 | 0 | 0 | v | 0 | 0 |
| *Staphylococcus Coag Neg* | step | 5 | v | v | 0 | 0 | v | 0 | 0 |
| *S. milleri* | stmi | 2 | 0, <grth | 0 | 0 | 0 | no growth | 0 | 0 |
| *S. pneumoniae* | stpn | 6 | 0, <grth | 0 | v | 0 | 0, <growth | 0 | 0 |
| *S pyogenes* | stpy | 6 | 0, <grth | 0 | v | v | +, <grth | 0 | 0 |
| | | 55 | | | | | | | |

+ = color detected
v = color varied slightly with strain
0 = no color detected
<= decreased growth vs. control

TABLE VI

| Colony Color on Various Chromogenic TSA II with 5% Sheep Blood (Detail) | | | | | | | | | | | | | | |
|---|---|---|---|---|---|---|---|---|---|---|---|---|---|---|
| Strain | Reference No. | Incub atm | Incub time | X-Acglm | M-Cap | Xgal/IPTG | X-Gal | X-Glucoside | X-Glucuro | Sal-Glucuro | Mag-Phos | X-Sulf | Mix | TSA control |
| aehy | 7965 | $CO_2$ | 21 h | gb | 0 | g | gb | 0 | NT | 0 | gp | 0 | pb | l yellow |
| aehy | 7966 | $CO_2$ | 21 h | gb | 0 | 0 | gb | g | NT | 0 | gp | 0 | pb | yellow |
| aehy | 49847 | $CO_2$ | 21 h | gb | 0 | lg | gb | gb | NT | 0 | g | 0 | pb | yellow |
| brca | 25238 | $CO_2$ | 21 h | 0 | 0 | 0 | 0 | 0 | NT | 0 | 0 | 0 | 0 | grey |
| brca | 25240 | $CO_2$ | 21 h | 0 | 0 | 0 | 0 | 0 | NT | 0 | p | 0 | 0 | l grey |
| caal | 10231 | $CO_2$ | 24 h | gb | 0 | 0 | 0 | 0 | NT | 0 | 0 | 0 | gb | grey |
| cakr | 34135 | $CO_2$ | 21 h | 0 | 0 | 0 | 0 | 0 | NT | 0 | lgp | 0 | 0 | grey |
| cifr | 8454 | $CO_2$ | 21 h | 0 | 0 | gb | gb | 0 | NT | 0 | 0 | 0 | 0 | grey |
| cifr | 33128 | $CO_2$ | 21 h | 0 | 0 | gb | gb | 0 | NT | 0 | 0 | gb | gp | grey |
| enfa | 597 | $CO_2$ | 21 h | db | 0 | 0 | 0 | b | NT | 0 | lp | 0 | db | grey |
| enfa | 10741 | $CO_2$ | 21 h | db | 0 | lgb | gb | db | NT | lp | 0 | db | grey | |
| enfa | 12953 | $CO_2$ | 21 h | db | 0 | 0 | 0 | db | NT | 0 | lp | 0 | b | grey |
| enfa | 14506 | $CO_2$ | 21 h | db | 0 | 0 | lgb | db | NT | 0 | lp | 0 | db | grey |
| enfa | 29212 | $CO_2$ | 21 h | db | 0 | gb | gb | db | NT | 0 | 0 | db | grey | |
| enfa | 29212 | $CO_2$ | 24 h | db | 0 | lgb | vlgb | b | NT | 0 | p | 0 | db | grey |
| enfu | 49032 | $CO_2$ | 21 h | db | 0 | 0 | gb | b | NT | 0 | vlgp | 0 | vlgp | grey |
| esco | 11775 | $CO_2$ | 21 h | 0 | 0 | b | b | 0 | NT | 0 | lp | 0 | gp | grey |
| esco | 25922 | $CO_2$ | 24 h | 0 | 0 | b | b | 0 | NT | 0 | lgb | 0 | b | grey |
| esco | 33605 | $CO_2$ | 21 h | 0 | 0 | gb | gb | 0 | NT | 0 | 0 | 0 | gp | grey |
| klpn | 13883 | $CO_2$ | 21 h | 0 | 0 | gb | gb | gb | NT | 0 | 0 | 0 | lp | grey (mucoid) |
| klpn | 33495 | $CO_2$ | 24 h | 0 | 0 | b | b | b | NT | 0 | p | 0 | b | grey |
| klpn | 33606 | $CO_2$ | 21 h | 0 | 0 | gb | gb | gb | NT | 0 | 0 | 0 | lp | grey |
| milu | 9341 | $CO_2$ | 21 h | 0 | 0 | 0 | 0 | 0 | NT | 0 | NG | 0 | 0 | l yellow |
| psae | 9027 | $CO_2$ | 21 h | 0 | 0 | 0 | 0 | 0 | NT | 0 | 0 | 0 | 0 | grey |
| psae | 15442 | $CO_2$ | 21 h | 0 | 0 | 0 | 0 | 0 | NT | 0 | 0 | 0 | 0 | yellow |
| psae | 33607 | $CO_2$ | 21 h | 0 | 0 | 0 | 0 | lgb | NT | 0 | 0 | 0 | 0 | l yellow |
| saty | 19430 | $CO_2$ | 21 h | 0 | 0 | 0 | 0 | 0 | NT | 0 | p | 0 | p | grey |
| satym | 14028 | $CO_2$ | 21 h | 0 | 0 | 0 | 0 | 0 | NT | 0 | p | 0 | p | grey |
| sema | 13880 | $CO_2$ | 21 h | gb | 0 | gb | gb | gb | NT | 0 | 0 | 0 | gb | grey |
| stag | 4768 | $CO_2$ | 21 h | 0 | 0 | 0 | 0 | b | NT | 0 | lp | 0 | lp | grey |
| stag | 12386 | $CO_2$ | 24 h | 0 | 0 | 0 | 0 | b | NT | gp | lp | 0 | p | white |
| stag | 12386 | $CO_2$ | 21 h | 0 | 0 | 0 | 0 | b | NT | 0 | p | 0 | p | white (beta) |
| stau | 25923 | $CO_2$ | 24 h | 0 | 0 | 0 | 0 | 0 | NT | 0 | lp | 0 | lp | white |
| stau | 1006 | $CO_2$ | 21 h | 0 | 0 | 0 | 0 | 0 | NT | 0 | 0 | 0 | 0 | white (beta) |
| stau | 1007 | $CO_2$ | 21 h | 0 | 0 | 0 | 0 | 0 | NT | 0 | 0 | 0 | 0 | white (beta) |
| stau | 1008 | $CO_2$ | 21 h | 0 | 0 | 0 | 0 | 0 | NT | 0 | vlp | 0 | vlp | white |
| stau | 1009 | $CO_2$ | 21 h | 0 | 0 | 0 | 0 | 0 | NT | 0 | vlp | 0 | vlp | white (beta) |
| step | 12228 | $CO_2$ | 21 h | 0 | 0 | 0 | 0 | 0 | NT | 0 | 0 | 0 | vlp | white |

TABLE VI-continued

| | | | | Colony Color on Various Chromogenic TSA II with 5% Sheep Blood (Detail) | | | | | | | | | | |
|---|---|---|---|---|---|---|---|---|---|---|---|---|---|---|
| Strain | Reference No. | Incub atm | Incub time | X-Acglm | M-Cap | Xgal/IPTG | X-Gal | X-Glucoside | X-Glucuro | Sal-Glucuro | Mag-Phos | X-Sulf | Mix | TSA control |
| step | cdc1 | $CO_2$ | 21 h | 0 | 0 | 0 | 0 | 0 | NT | 0 | lp | 0 | lp | grey |
| step | cdc2 | $CO_2$ | 21 h | 0 | 0 | 0 | 0 | 0 | NT | 0 | 0 | 0 | 0 | white |
| step | cdc3 | $CO_2$ | 21 h | 0 | 0 | b | b | 0 | NT | 0 | 0 | 0 | 0 | white |
| step | cdc4 | $CO_2$ | 21 h | 0 | 0 | 0 | 0 | 0 | NT | 0 | lp | 0 | 0 | grey |
| stmi | 6249 | $CO_2$ | 21 h | NG | 0 | 0 | 0 | 0 | NT | 0 | NG | NG | NG | NG |
| stpn | 6303 | $CO_2$ | 24 h | 0 | 0 | 0 | 0 | 0 | NT | 0 | 0 | 0 | 0 | alpha |
| stpn | 6305 | $CO_2$ | 24 h | 0 | 0 | 0 | 0 | 0 | NT | 0 | 0 | 0 | 0 | alpha |
| stpn | 1259 | $CO_2$ | 21 h | 0 | 0 | 0 | 0 | 0 | NT | 0 | 0 | 0 | 0 | alpha (mucoid) |
| stpn | 1260 | $CO_2$ | 21 h | 0 | 0 | 0 | 0 | 0 | NT | 0 | 0 | 0 | NG | alpha |
| stpn | 1331 | $CO_2$ | 21 h | 0 | 0 | 0 | NG | NG | NT | NG | NG | NG | NG | NG |
| stpn | 1628 | $CO_2$ | 21 h | 0 | 0 | 0 | 0 | 0 | NT | 0 | 0 | 0 | 0 | alpha |
| stpy | 19615 | $CO_2$ | 21 h | 0 | 0 | 0 | 0 | gb | NT | 0 | lp | 0 | lp | white (beta) |
| stpy | 49117 | $CO_2$ | 21 h | 0 | 0 | 0 | 0 | 0 | NT | 0 | lp | 0 | lp | white (beta) |
| stpy | 51339 | $CO_2$ | 21 h | 0 | 0 | 0 | 0 | 0 | NT | 0 | lp | 0 | lp | white (beta) |
| stpy | 1027 | $CO_2$ | 21 h | 0 | 0 | 0 | 0 | 0 | NT | 0 | vlp | 0 | vlp | NG |
| stpy | 1028 | $CO_2$ | 21 h | 0 | 0 | 0 | 0 | lgb | NT | 0 | vlp | 0 | vlp | grey (beta) |
| stpy | 1029 | $CO_2$ | 21 h | 0 | 0 | 0 | 0 | lgb | NT | 0 | vlp | 0 | vlp | NG |
| stpy | 1030 | $CO_2$ | 21 h | 0 | 0 | 0 | 0 | gb | NT | 0 | vlp | 0 | vlp | grey (beta) |
| caal | 10231 | air | 24 h | 0 | 0 | 0 | 0 | 0 | NT | 0 | 0 | 0 | 0 | grey (darker) |
| enfa | 597 | air | 21 h | b | 0 | 0 | 0 | b | NT | 0 | lp | 0 | db | grey |
| enfa | 10741 | air | 21 h | b | 0 | lb | lgb | b | NT | 0 | p | 0 | db | grey |
| enfa | 12953 | air | 21 h | b | 0 | 0 | 0 | b | NT | 0 | p | 0 | db | grey |
| enfa | 14506 | air | 21 h | b | 0 | 0 | 0 | b | NT | 0 | p | 0 | db | grey |
| enfa | 29212 | air | 21 h | b | 0 | lgb | gb | b | NT | 0 | p | 0 | db | grey |
| enfa | 29212 | air | 24 h | db | 0 | lgb | vlgb | b | NT | 0 | p | 0 | db | grey |
| enfu | 49032 | air | 21 h | lb | 0 | 0 | db | b | NT | 0 | lgp | 0 | lp (gb48h) | grey |
| esco | 25922 | air | 24 h | 0 | 0 | b | b | 0 | NT | 0 | lgb | 0 | b | grey |
| klpn | 33495 | air | 24 h | 0 | 0 | b | b | b | NT | 0 | p | 0 | b | grey |
| stag | 4768 | air | 21 h | 0 | 0 | 0 | 0 | lb | NT | 0 | p | 0 | lp | grey |
| stag | 12386 | air | 24 h | 0 | 0 | 0 | 0 | b | NT | gp | lp | 0 | p | grey |
| stau | 25923 | air | 24 h | 0 | 0 | 0 | 0 | 0 | NT | 0 | lp | 0 | lp | white |
| step | 12228 | air | 21 h | 0 | 0 | 0 | 0 | 0 | NT | 0 | lp | 0 | 0 (p-48h) | white |
| step | cdc1 | air | 21 h | 0 | 0 | 0 | 0 | 0 | NT | 0 | lp | 0 | lp | grey |
| step | cdc2 | air | 21 h | 0 | 0 | 0 | 0 | 0 | NT | 0 | 0 | 0 | 0 | white |
| step | cdc3 | air | 21 h | lb | 0 | b | b | 0 | NT | 0 | 0 | 0 | 0 | white |
| step | cdc4 | air | 21 h | 0 | 0 | 0 | 0 | 0 | NT | 0 | lp | 0 | vlp | grey |
| stmi | 6249 | air | 21 h | 0 | 0 | 0 | 0 | 0 | NT | 0 | 0 | 0 | NG | NG |
| stpn | 6303 | air | 24 h | 0 | 0 | 0 | 0 | 0 | NT | 0 | db | 0 | 0 | alpha |
| stpn | 6305 | air | 24 h | 0 | 0 | 0 | 0 | 0 | NT | 0 | 0 | 0 | 0 | alpha |
| stpy | 19615 | air | 21 h | 0 | 0 | 0 | 0 | lgb | NT | 0 | lp | 0 | lgb (p48h) | white (beta) |
| stpy | 49117 | air | 21 h | 0 | 0 | 0 | 0 | 0 | NT | 0 | p | 0 | lp | white (beta) |
| stpy | 51339 | air | 21 h | 0 | 0 | 0 | 0 | lgb | NT | 0 | p | 0 | lp | white (beta) |
| aehy | 7965 | $CO_2$ | 18 h | db | NT | NT | NT | 0 | 0 | NT | NT | NT | NT | grey hem |
| aehy | 7966 | $CO_2$ | 18 h | db | NT | NT | NT | 0 | 0 | NT | NT | NT | NT | grey hem |
| aehy | 49847 | $CO_2$ | 18 h | db | NT | NT | NT | gb | 0 | NT | NT | NT | NT | grygrn hem |
| brca | 25238 | $CO_2$ | 18 h | 0 | NT | NT | NT | 0 | 0 | NT | NT | NT | NT | grey |
| brca | 25240 | $CO_2$ | 18 h | NG | NT | NT | NT | 0 | 0 | NT | NT | NT | NT | grey |
| caal | 10231 | $CO_2$ | 18 h | b | NT | NT | NT | 0 | 0 | NT | NT | NT | NT | grey |
| cakr | 34135 | $CO_2$ | 18 h | 0 | NT | NT | NT | 0 | 0 | NT | NT | NT | NT | grey |
| cifr | 8454 | $CO_2$ | 18 h | 0 | NT | NT | NT | 0 | 0 | NT | NT | NT | NT | dark grey |
| cifr | 33128 | $CO_2$ | 18 h | 0 | NT | NT | NT | 0 | 0 | NT | NT | NT | NT | grey |
| enfa | 597 | $CO_2$ | 18 h | db | NT | NT | NT | db | 0 | NT | NT | NT | NT | grey |
| enfa | 10741 | $CO_2$ | 18 h | db | NT | NT | NT | db | 0 | NT | NT | NT | NT | grey |
| enfa | 12953 | $CO_2$ | 18 h | db | NT | NT | NT | db | 0 | NT | NT | NT | NT | grey |
| enfa | 14506 | $CO_2$ | 18 h | db | NW | NT | NT | db | 0 | NT | NT | NT | NT | grey |
| enfa | 29212 | $CO_2$ | 18 h | db | NT | NT | NT | db | 0 | NT | NT | NT | NT | grey |
| enfu | 49032 | $CO_2$ | 18 h | lb | NT | NT | NT | db | 0 | NT | NT | NT | NT | grey |
| esco | 11775 | $CO_2$ | 18 h | 0 | NT | NT | NT | 0 | b | NT | NT | NT | NT | grey |
| esco | 33605 | $CO_2$ | 18 h | 0 | NT | NT | NT | 0 | b | NT | NT | NT | NT | grey hem |
| klpn | 13883 | $CO_2$ | 18 h | 0 | NT | NT | NT | b | 0 | NT | NT | NT | NT | white grey |
| klpn | 33495 | $CO_2$ | 18 h | vlgb | NT | NT | NT | gb | 0 | NT | NT | NT | NT | white grey |
| klpn | 33606 | $CO_2$ | 18 h | 0 | NT | NT | NT | gb | 0 | NT | NT | NT | NT | white grey |
| miiu | 9341 | $CO_2$ | 18 h | ly | NT | NT | NT | ly | ly | NT | NT | NT | NT | lt yellow |
| psae | 9027 | $CO_2$ | 18 h | 0 | NT | NT | NT | 0 | 0 | NT | NT | NT | NT | dark grey |
| psae | 15442 | $CO_2$ | 18 h | 0 | NT | NT | NT | 0 | 0 | NT | NT | NT | NT | dark grey |
| psae | 33607 | $CO_2$ | 18 h | 0 | NT | NT | NT | 0 | 0 | NT | NT | NT | NT | dark grey |
| saty | 19430 | $CO_2$ | 18 h | 0 | NT | NT | NT | 0 | 0 | NT | NT | NT | NT | grey |
| satym | 14028 | $CO_2$ | 18 h | 0 | NT | NT | NT | 0 | 0 | NT | NT | NT | NT | dark grey |

TABLE VI-continued

| | | | | Colony Color on Various Chromogenic TSA II with 5% Sheep Blood (Detail) | | | | | | | | | | |
|---|---|---|---|---|---|---|---|---|---|---|---|---|---|---|
| Strain | Reference No. | Incub atm | Incub time | X-Acglm | M-Cap | Xgal/IPTG | X-Gal | X-Glucoside | X-Glucuro | Sal-Glucuro | Mag-Phos | X-Sulf | Mix | TSA control |
| sema | 13880 | $CO_2$ | 18 h | gb | NT | NT | NT | bg | 0 | NT | NT | NT | NT | dark grey |
| stau | 25923 | $CO_2$ | 18 h | 0 | NT | NT | NT | 0 | 0 | NT | NT | NT | NT | white |
| stau | t006 | $CO_2$ | 18 h | 0 | NT | NT | NT | 0 | 0 | NT | NT | NT | NT | white |
| stau | t007 | $CO_2$ | 18 h | 0 | NT | NT | NT | 0 | 0 | NT | NT | NT | NT | white |
| stau | t008 | $CO_2$ | 18 h | 0 | NT | NT | NT | 0 | 0 | NT | NT | NT | NT | white |
| stau | t009 | $CO_2$ | 18 h | 0 | NT | NT | NT | 0 | 0 | NT | NT | NT | NT | white |
| step | 12228 | $CO_2$ | 18 h | 0 | NT | NT | NT | 0 | 0 | NT | NT | NT | NT | white |
| step | cdc1 | $CO_2$ | 18 h | 0 | NT | NT | NT | 0 | 0 | NT | NT | NT | NT | white |
| stha | cdc2 | $CO_2$ | 18 h | 0 | NT | NT | NT | 0 | 0 | NT | NT | NT | NT | white |
| stsa | cdc3 | $CO_2$ | 18 h | 0 | NT | NT | NT | 0 | 0 | NT | NT | NT | NT | white |
| step | cdc4 | $CO_2$ | 18 h | 0 | NT | NT | NT | 0 | 0 | NT | NT | NT | NT | white beta |
| stmi | 6242 | $CO_2$ | 18 h | 0 | NT | NT | NT | 0 | 0 | NT | NT | NT | NT | alpha |
| stpn | t259 | $CO_2$ | 18 h | 0 | NT | NT | NT | 0 | 0 | NT | NT | NT | NT | alpha |
| stpn | t260 | $CO_2$ | 18 h | 0 | NT | NT | NT | 0 | 0 | NT | NT | NT | NT | alpha |
| stpn | t331 | $CO_2$ | 18 h | drkr<muc | NT | NT | NT | 0 | 0 | NT | NT | NT | NT | alpha muc |
| stpn | t628 | $CO_2$ | 18 h | 0 | NT | NT | NT | bg | 0 | NT | NT | NT | NT | alpha |
| stpy | 51339 | $CO_2$ | 18 h | 0 | NT | NT | NT | 0 | db beta | NT | NT | NT | NT | beta |
| stpy | t027 | $CO_2$ | 18 h | 0 | NT | NT | NT | 0 | 0 | NT | NT | NT | NT | beta |
| stpy | t028 | $CO_2$ | 18 h | 0 | NT | NT | NT | 0 | 0 | NT | NT | NT | NT | beta |
| stpy | t029 | $CO_2$ | 18 h | 0 | NT | NT | NT | 0 | 0 | NT | NT | NT | NT | beta |
| stpy | t030 | $CO_2$ | 18 h | 0 | NT | NT | NT | lgb | 0 | NT | Nt | NT | NT | beta |

Strain Abbreviation as defined in Table V
NG = Growth
NT = Not tested
0 = No Color
alpha = alpha hemolysis
beta = beta hemolysis Again, it was surprising to discover that chromogenic substrates applied to the surface of, or incorporated within a highly colored medium (i.e., a nutrient medium containing blood or hemin) could help to identify and/or differentiate microorganisms.

As will be observed from review of the data tabulated above, Group B Strep (3 of 3 strains) gave blue colonies on X-glucoside TSA II. Colony hemolytic activity was slightly reduced. The CAMP test works well on X-glucoside TSA II (as described in the Manual of BBL® Products and Laboratory Procedures). PYR test (as described in Manual of Clinical Microbiology, 6th ed., P. R. Murray, E. J. Baron, M. A. Pfaller, F. C. Tenover and R. H. Yolken, 1995 ASM Press, Washington, D.C.) would be needed to rule out *S. pyogenes* or Group D strep which may also be blue. 4 of 7 *S. pyogenes* gave light grey blue color. 7 of 7 Enterococcus gave a blue color.

Group D Strep (7 of 7 strains) gave dark blue colonies on X-Acglmn. A few Gram Negative strains, one *C. albicans* and one *S. epidermidis* also gave blue colonies.

$CO_2$ incubations typically gave slightly stronger color reactions vs. air incubation for all chromogens.

Addition of the X-chromogens prior to autoclaving did not effect performance.

M-Cap and X-Sulf were inactive for most organisms. Literature suggests that sodium desoxycholate may be important for the M-Cap reaction with Salmonella spp. One strain of Citrobacter gave a grey blue with X-Sulf TSA II.

Some of the chromogens, especially magenta substrates, caused the blood agar to darken after incubation, particularly after $CO_2$ incubation. This darkening of the plate reduced the readability of the purple color reactions and hemolytic reactions.

X-gal was not particularly useful for Gram-positives. IPTG appeared to reduce the reactivity for some strains with X-gal. *E. faecium* (ATCC 49032) gave dark blue on X-Gal but no color on X-Gal with IPTG.

As would be expected, chromogens that produced colony colors that clearly contrast with the red surface of the blood plate are optimal. The blue-chromogen, X-substrate (5-bromo-4-chloro-3-indoxyl) has an absorption max (nm) of 615 which is most differentiated from the red blood plates color of approx. 515 nm. Some chromogens which produce purple/red/magenta colonies are not as easy to read against the red blood plate background.

Based on the above data, the color contrast can be summarized as follows:

| Chromogen | Abbr. | Colony | Absorption max (nm) | Contrast on Blood Plate |
|---|---|---|---|---|
| 5-Bromo-4-chloro-3-indoxyl | X- | blue | 615 | Good |
| 5-Bromo-6-chloro-3-indoxyl | Mag- | purple/red | 565 | Fair/poor |
| 6-chloro-3-indoxyl | Sal- | grey purple | 540 | Poor* |

*Compound unstable, gave poor reactions with positive control (*E. coli* 25922)

While the examples use TSASB and chocolate agar as the blood or hemin containing culture media, the invention is not limited to these two media.

It is expected that other, similar blood or hemin containing media, such as Columbia Agar Base, with the addition of blood, which is widely used in Europe, would also be useful in the present invention. This media is commercially available, and contains more amino acid and carbohydrate than TSASB.

It is noted, however, that limited efforts to use commercially available Brucella Agar with blood, produced bacterial growth but no color change.

The above Examples are intended to be purely exemplary, and are not intended to in any way limit the scope of the present invention.

What we claim is:

1. A method for differentiating microorganisms in a sample comprising:

(a) growing said microorganisms on a chromogenic indicator medium which comprises:

(i) a nutrient containing blood or hemin; and (ii) a chromogen; and (b) detecting a color change among the microorganisms grown.

2. The method according to claim 1 wherein component (i) of said chromogenic indicator medium is Trypticase Soy Agar and Blood.

3. The method according to claim 1 wherein component (i) of said chromogenic indicator medium is chocolate agar.

4. The method according to claim 1 wherein said microorganisms are bacteria.

5. The method according to claim 1 wherein said microorganisms are yeasts.

6. The method according to claim 1 wherein the microorganisms are obtained from a clinical source.

7. The method according to claim 1 wherein the microorganisms are obtained from an industrial source.

8. The method according to claim 1 wherein the microorganisms are obtained from a food source.

9. The method according to claim 1 wherein the chromogen is an X-linked chromogen.

10. The method according to claim 1 wherein the chromogen is a Magenta-linked chromogen.

11. The method according to claim 1 wherein the chromogen is a fluorogenic chromogen.

12. The method according to claim 1 wherein the chromogen has an absorption maximum of between about 400 nm and 800 nm.

13. The method according to claim 11 wherein the chromogen has an absorption maximum of between about 10 nm and 400 nm.

14. The method according to claim 3 wherein the microorganisms are bacteria.

15. The method according to claim 14 wherein the bacteria are obtained from a clinical source.

16. The method according to claim 14 wherein the bacteria are obtained from an industrial source.

17. The method according to claim 14 wherein the bacteria are obtained from a food source.

18. The method according to claim 14 wherein the chromogen is an X-linked chromogen.

19. The method according to claim 14 wherein the chromogen is a Magenta-linked chromogen.

20. The method according to claim 14 wherein the chromogen is a fluorogenic chromogen.

21. The method according to claim 14 wherein the chromogen has an absorption maximum of between about 400 nm and 800 nm.

22. The method according to claim 20 wherein the chromogen has an absorption maximum of between 10 nm and 400 nm.

23. A method for differentiating microorganisms in a sample comprising: a) applying a sample suspected of containing microorganisms of interest to a chromogenic indicator medium comprising (i) a nutrient containing blood or hemin; and (ii) a chromogen; b) incubating the sample for a period sufficient to permit detectable growth; and c) determining the visible presence or absence of microorganisms of interest.

24. The method according to claim 23 wherein component (i) of said chromogenic indicator medium is Trypticase Soy Agar and Blood.

25. The method according to claim 23 wherein component (i) of said chromogenic indicator medium is chocolate agar.

26. The method according to claim 23 wherein said microorganisms are bacteria.

27. The method according to claim 26 wherein said bacteria is *Haemophilus influenzae.*

28. The method according to claim 23 wherein said microorganisms are yeasts.

29. The method according to claim 23 wherein the microorganisms are obtained from a clinical source.

30. The method according to claim 23 wherein the microorganisms are obtained from an industrial source.

31. The method according to claim 23 wherein the microorganisms are obtained from a food source.

32. The method according to claim 23 wherein the chromogen is an X-linked chromogen.

33. The method according to claim 23 wherein the chromogen is a Magenta-linked chromogen.

34. The method according to claim 33 wherein said Magenta-linked chromogen is Magenta-phosphate.

35. The method according to claim 23 wherein the chromogen is a fluorogenic chromogen.

36. The method according to claim 23 wherein the chromogen has an absorption maximum of between about 400 nm and 800 nm.

37. The method according to claim 35 wherein the chromogen has an absorption maximum of between 10 nm and 400 nm.

38. A method of preparing chromogenic media containing blood or hemin comprising applying a chromogenic substrate to a surface of a previously prepared nutrient media, wherein the chromogenic substrate is carried in a solvent.

39. A method of preparing chromogenic media containing blood or hemin comprising adding a chromogenic substrate to a culture medium when the culture medium is prepared and prior to distribution to plates or tubes.

* * * * *